(12) United States Patent
Guo et al.

(10) Patent No.: US 11,774,423 B1
(45) Date of Patent: Oct. 3, 2023

(54) PARALLEL DEVICE AND METHOD FOR HIGH-PRECISION DETERMINATION OF SULFUR SOLUBILITY UNDER MULTIPLE INFLUENCING FACTORS

(71) Applicant: Southwest Petroleum University, Chengdu (CN)

(72) Inventors: Xiao Guo, Chengdu (CN); Binliang Jiang, Chengdu (CN); Jingjing Ma, Chengdu (CN); Tao Li, Chengdu (CN); Pengkun Wang, Chengdu (CN); Changqing Jia, Chengdu (CN); Ming Zhou, Chengdu (CN); Yi He, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 18/089,618

(22) Filed: Dec. 28, 2022

(30) Foreign Application Priority Data

Jun. 28, 2022 (CN) .......................... 202210751472.5

(51) Int. Cl.
G01N 33/00 (2006.01)
G01N 5/02 (2006.01)
G01M 3/02 (2006.01)

(52) U.S. Cl.
CPC .......... G01N 33/0044 (2013.01); G01M 3/02 (2013.01); G01N 5/02 (2013.01)

(58) Field of Classification Search
CPC .............................. G01N 33/0044; G01N 5/02
See application file for complete search history.

(56) References Cited

U.S. PATENT DOCUMENTS

2017/0191972 A1* 7/2017 Sherik ..................... G01G 19/00
2020/0132647 A1* 4/2020 Wang ................. G01N 33/0036

FOREIGN PATENT DOCUMENTS

| CN | 104568678 A | * | 4/2015 |
| CN | 106124354 A | | 11/2016 |
| CN | 108474776 A | | 8/2018 |

(Continued)

OTHER PUBLICATIONS

CN-113970588-A—Translate (Year: 2022).*

(Continued)

*Primary Examiner* — Kristina M Deherrera
*Assistant Examiner* — Fatemeh Esfandiari Nia
(74) *Attorney, Agent, or Firm* — Nitin Kaushik

(57) ABSTRACT

The invention discloses a parallel device and method for high-precision determination of sulfur solubility under multiple influencing factors, and the device comprises an elemental sulfur absorption system, an elemental sulfur saturation system and a sulfur content determination system. The elemental sulfur absorption system is used to remove the dissolved elemental sulfur in the sour gas. The elemental sulfur saturation system is arranged in parallel to saturate sour gases at different temperatures and pressures at the same time. The elemental sulfur absorption system and the elemental sulfur saturation system are arranged in parallel. The sulfur content determination system is used to determine the total sulfur content of the parallel elemental sulfur saturation system and the elemental sulfur content in the sour gas after absorbing the elemental sulfur under the same conditions.

10 Claims, 4 Drawing Sheets

(56) References Cited

FOREIGN PATENT DOCUMENTS

| CN | 108878816 | A |   | 11/2018 |          |
|----|-----------|---|---|---------|----------|
| CN | 111272621 | A | * | 6/2020  |          |
| CN | 112014261 | A | * | 12/2020 | G01N 5/02 |
| CN | 113970588 | A | * | 1/2022  |          |

OTHER PUBLICATIONS

CN-112014261-A—Translate (Year: 2020).*
CN-111272621-A—Translae (Year: 2020).*
CN-104568678-A—Translate (Year: 2015).*

* cited by examiner

PARALLEL DEVICE AND METHOD FOR HIGH-PRECISION DETERMINATION OF SULFUR SOLUBILITY UNDER MULTIPLE INFLUENCING FACTORS

CROSS-REFERENCE TO RELATED APPLICATIONS

The application claims priority to Chinese patent application No. 2022107514725, filed on Jun. 28, 2022, the entire contents of which are incorporated herein by reference.

TECHNICAL FIELD

The present invention pertains to the technical field of solubility determination of sour gas, and in particular to a parallel device and method for the high-precision determination of sulfur solubility under multiple influencing factors.

BACKGROUND

In recent years, a number of sour gas reservoirs have been developed and put into production in China. During drilling and production, sour gas flows from the porous formation to the bottom of the well and flows to the wellhead. During the rising process, the state of sour gas changes with the decrease of temperature and pressure, during which the solubility of gaseous sulfur in the fluid decreases, leading to precipitation and condensation and forming some droplets that are adsorbed on the rock surface or flow with sour gas. After cooling, the flowing droplets become solid particles and are deposited. These particles will be settled in the formation or pipeline, blocking the formation pores, reducing the formation permeability, and seriously affecting the production of natural gas.

The calculation of elemental sulfur solubility in sour gas is the key to sulfur deposition prediction, but the existing sulfur solubility determination devices cannot quickly determine the sulfur solubility of sour gas at different temperatures, pressures and any gas sample conditions, and can only determine the sulfur solubility of sour gas at single temperature or pressure each time. In addition, in the process of stirring inside the sample preparation chamber, the sample is not mixed uniformly enough, which reduces the detection effect.

SUMMARY

In response to the above problems, the present invention aims to provide a parallel device and method for the high-precision determination of sulfur solubility under multiple influencing factors, which can simultaneously and rapidly determine the total amount of elemental sulfur in a sour gas sample under different temperature and pressure conditions, and then calculate the sulfur solubility in the sour gas sample, and acquire the sulfur solubility data under multi-point conditions by a single determination.

The technical solution of the present invention is as follows;

On the one hand, the present invention provides a parallel device for high-precision determination of sulfur solubility under multiple influencing factors, comprising a sample preparation system, an elemental sulfur absorption system, an elemental sulfur saturation system, a sulfur content determination system, a vacuum pumping system, and a nitrogen filling and replacement system; the elemental sulfur absorption system is used to absorb the elemental sulfur of sour gas, and arranged in an incubator I (62); the elemental sulfur saturation system, arranged in an incubator II (63), comprises multiple elemental sulfur saturation subsystems arranged in parallel, and the subsystems are used to saturate sour gas under different temperature and pressure conditions at the same time; the elemental sulfur absorption system is arranged in parallel with the elemental sulfur saturation system, with the input terminals of both are connected with the output terminal of the sample preparation system, and the output terminals of both connected with the input terminal of the sulfur content determination system; the sulfur content determination system is used to determine the total sulfur content of the elemental sulfur saturation system, and calibrate the elemental sulfur content in the sour gas after the elemental sulfur absorption system absorbs the elemental sulfur under the same conditions as the elemental sulfur saturation system; the vacuum pumping system is used to make the whole device vacuum to remove impurities; the nitrogen filling and replacement system is used to fill the entire device with nitrogen to test the air tightness of the device and blow the elemental sulfur precipitated in the pipe into the sulfur content determination system.

Preferably, the sample preparation system comprises gas cylinders, gas cylinder valves, a constant speed and constant pressure (CSCP) pump I, a gas flowmeter I, a gas booster pump I, a one-way valve I, a gas sample preparation chamber, a gas sample preparation chamber valve, and a gas booster pump II, which are connected in turn; the gas cylinders comprise a hydrogen sulfide cylinder, a carbon dioxide cylinder, and a methane cylinder arranged in parallel; the gas cylinder valves comprise a hydrogen sulfide cylinder valve, a carbon dioxide cylinder valve, and a methane cylinder valve; the gas sample preparation chamber is connected with a pressure gauge I;

The elemental sulfur absorption system comprises a one-way valve II, an intermediate container, an intermediate container valve, a gas booster pump III, an elemental sulfur absorption chamber, an absorption chamber valve, a gas dryer, a CSCP pump II, and a gas flowmeter II, which are connected in turn; the intermediate container is connected to a pressure gauge II, the elemental sulfur absorption chamber is connected to a pressure gauge III, and the elemental sulfur absorption chamber is provided with a chemical agent for absorbing elemental sulfur;

The elemental sulfur saturation system comprises a one-way valve III, a gas preheating chamber, a gas booster pump IV, three groups of elemental sulfur saturation subsystems arranged in parallel, which are connected in turn; each group of sulfur saturation subsystem comprises a one-way valve, an HTHP sample preparation chamber, a sample preparation chamber valve, a sulfur powder filter, a CSCP pump, and a gas flowmeter, which are connected in turn; the gas preheating chamber is provided with an electromagnetic strip heater I, the HTHP sample preparation chamber is provided with an electromagnetic strip heater II, and the HTHP sample preparation chamber is connected with a pressure gauge;

The sulfur content determination system comprises a fluorescence sulfur analyzer and a tail gas treatment device which are connected in turn; the input terminal of fluorescence sulfur analyzer is connected with the output terminal respectively of elemental sulfur absorption system and elemental sulfur saturation system;

The vacuum pumping system comprises a vacuum pump of which the output terminal is connected with the output terminal of the elemental sulfur absorption system by a pipeline I that is provided with a vacuum pump valve I; the output terminal of the vacuum pump is connected with the output terminal of the elemental sulfur saturation system by a pipeline H which is provided with a vacuum pump valve II;

The nitrogen filling and replacement system comprises a nitrogen cylinder I and a nitrogen cylinder II; the nitrogen cylinder I is used to fill the entire device with nitrogen to test the air tightness of the device, and the nitrogen cylinder II is used to blow the elemental sulfur precipitated in the pipe into the sulfur content determination system; the nitrogen cylinder I is connected with the pipeline between the gas flowmeter and the gas booster pump I via a pipeline III which is provided with a nitrogen valve I; the nitrogen cylinder II is connected with the output terminal respectively of the elemental sulfur absorption system and the elemental sulfur saturation system through a pipeline IV which is provided with a nitrogen valve H.

Preferably, the elemental sulfur absorption chamber is internally provided with carbon disulfide.

Preferably, the effective volumes of the gas preparation chamber, the HTHP preparation chamber, the intermediate container, and the elemental sulfur absorption chamber are reduced in turn, and the volume of the next container is not greater than ⅓ of that of the previous container.

Preferably, the sample preparation chamber comprises a seal housing provided with a stirring device, the side wall of the seal housing is provided with an intake pipe and an outlet pipe which are connected inside of the seal housing, the sealing shell is internally provided with a connecting pipe with one terminal connected with the output terminal of the intake pipe, and the connecting pipe is provided with a plurality of evenly distributed air vents.

Preferably, the seal housing is provided with a fixed base at the bottom.

Preferably, the seal housing is provided with a transparent window on the side wall.

Preferably, the stirring device comprises a motor, the output terminal of the motor is provided with a rotating rod of which the side wall is equipped with a plurality of stirring blades and the bottom is connected with the top of the link block; the left and right ends of the bottom of the link block are respectively provided with a limit rod that is fitted with a fixed cylinder internally, the fixed barrel is provided with a vertical rod with other terminals passing through the fixed cylinder and extending towards the link block, the top of the vertical rod is provided with a limit slider that is provided with a spring, the left and right ends of the bottom of the vertical rod are hinged with the movable plates, the upper surfaces of the two movable plates are respectively designed with a chute, and the limit rod is limited to slide in the chute.

On the other hand, the present invention also provides a method for high-precision determination of sulfur solubility under multiple influencing factors, the parallel device for high-precision determination of sulfur solubility under multiple influencing factors described in any one of above items is used for determination, comprising the following steps:

Prepare the sour gas to be determined with the sample preparation system, and then determine the sulfur content I of sour gas to be determined after sulfur absorption and the volume of hydrogen sulfide gas through the path of sample preparation system, elemental sulfur absorption system and sulfur content determination system;

Prepare the same sour gas to be determined with the sample preparation system, and then determine the sulfur content II of sour gas to be determined after sulfur saturation at different temperatures and pressures through the path of sample preparation system, elemental sulfur saturation system and sulfur content determination system;

Work out the solubility of the sour gas to be determined by calculating the sulfur content I, sulfur content II and the volume of hydrogen sulfide gas.

Preferably, the solubility is calculated by the following equation:

$$R = \frac{M - m}{V} \tag{1}$$

Where, R is the solubility of sour gas to be determined; m is the sulfur content I of sour gas to be determined after removal of elemental sulfur; M is the sulfur content II of sour gas to be determined after the saturation of sulfur monomer; V is the volume of sour gas sample.

The present invention has the following beneficial effects:

By setting up the elemental sulfur absorption system and the elemental sulfur saturation system, the present invention can accurately calculate the sulfur solubility of sour gas by comparing gas volume based on the sulfur content difference between the sour gas sample of saturated sulfur powder and the sour gas sample after sulfur absorption, so as to make the sulfur solubility determination of sour gas safer and more efficient and convenient, and provide data support for the recovery efficiency of sour gas reservoir.

BRIEF DESCRIPTION OF DRAWINGS

In order to explain the embodiments of the present invention or the technical solutions in the prior art more clearly, the following will make a brief introduction to the drawings needed in the description of the embodiments or the prior art. Obviously, the drawings in the following description are merely some embodiments of the present invention. For those of ordinary skill in the art, other drawings can be obtained based on the structures shown in these drawings without any creative effort.

EXPLANATION OF NUMBERS MARKED IN THE FIGURE

1—hydrogen sulfide cylinder, 2—carbon dioxide cylinder, 3—methane cylinder, 4—hydrogen sulfide cylinder valve, 5—carbon dioxide cylinder valve, 6—methane cylinder valve, 7—constant speed and constant pressure pump I, 8—gas flowmeter I, 9—nitrogen cylinder I, 10—nitrogen valve I, 11—gas booster pump I. 12—one-way valve I, 13—pressure gauge I, 14—gas sample preparation chamber, 1401—transparent window. 1402—fixed base, 1403—limit slider, 1404 gas inlet pipe, 1405—gas outlet pipe, 1406—connecting pipe, 1407—support plate, 1408—motor, 1409—rotating rod, 1410—stirring blade, 1411—link block, 1412—fixed cylinder, 1413—vertical rod, 1414—limit rod, 1415—spring, 1416—movable plate, 15—gas sample preparation chamber valve, 16—gas booster pump II, 17—one-way valve II, 18—pressure gauge II, 19—intermediate container, 20—intermediate container valve. 21—gas booster pump III, 22—elemental sulfur absorption chamber, 23—pressure gauge III, 24—absorption chamber valve, 25—gas dryer, 26-constant speed and constant pressure pump II, 27—one-way valve III, 28—electromagnetic strip heater I, 29—gas preheating chamber, 30—gas booster pump IV, 31—one-way valve IV, 32-one-way valve V, 33—one-way valve VI, 34—pressure gauge IV, 35—pressure gauge V, 36-pressure gauge VI. 37—high temperature and high pressure chamber I, 38—high temperature and high pressure chamber II, 39—high temperature and high pressure chamber III, 40—sample preparation chamber valve I, 41—sample preparation chamber valve II, 42—sample preparation chamber valve III, 43—sulfur powder filter I, 44—sulfur powder filter II, 45—sulfur powder filter III, 46—constant speed and constant pressure pump III, 47—constant speed and constant pressure pump III, 48—constant speed and pressure pump V, 49—gas flowmeter III, 50—gas flowmeter IV, 51—gas flowmeter V, 52—vacuum pump valve II, 53—vacuum pump, 54—vacuum pump valve I, 55—one-way valve VIII, 56—one-way valve LX, 57—nitrogen valve II, 58—nitrogen cylinder II, 59—fluorescence sulfur analyzer, 60—tail gas treatment device, 61—gas flowmeter II, 62—incubator I, 63—incubator II.

DETAILED DESCRIPTION OF THE EMBODIMENTS

The present invention is further described with reference to the drawings and embodiments. It should be noted that the embodiments in this application and the technical features in the embodiments can be combined with each other without conflict. It is to be noted that, unless otherwise specified, all technical and scientific terms herein have the same meaning as commonly understood by those of ordinary skill in the art to which this application belongs. "Include" or "comprise" and other similar words used in the present disclosure mean that the components or objects before the word cover the components or objects listed after the word and its equivalents, but do not exclude other components or objects.

Figure 1:
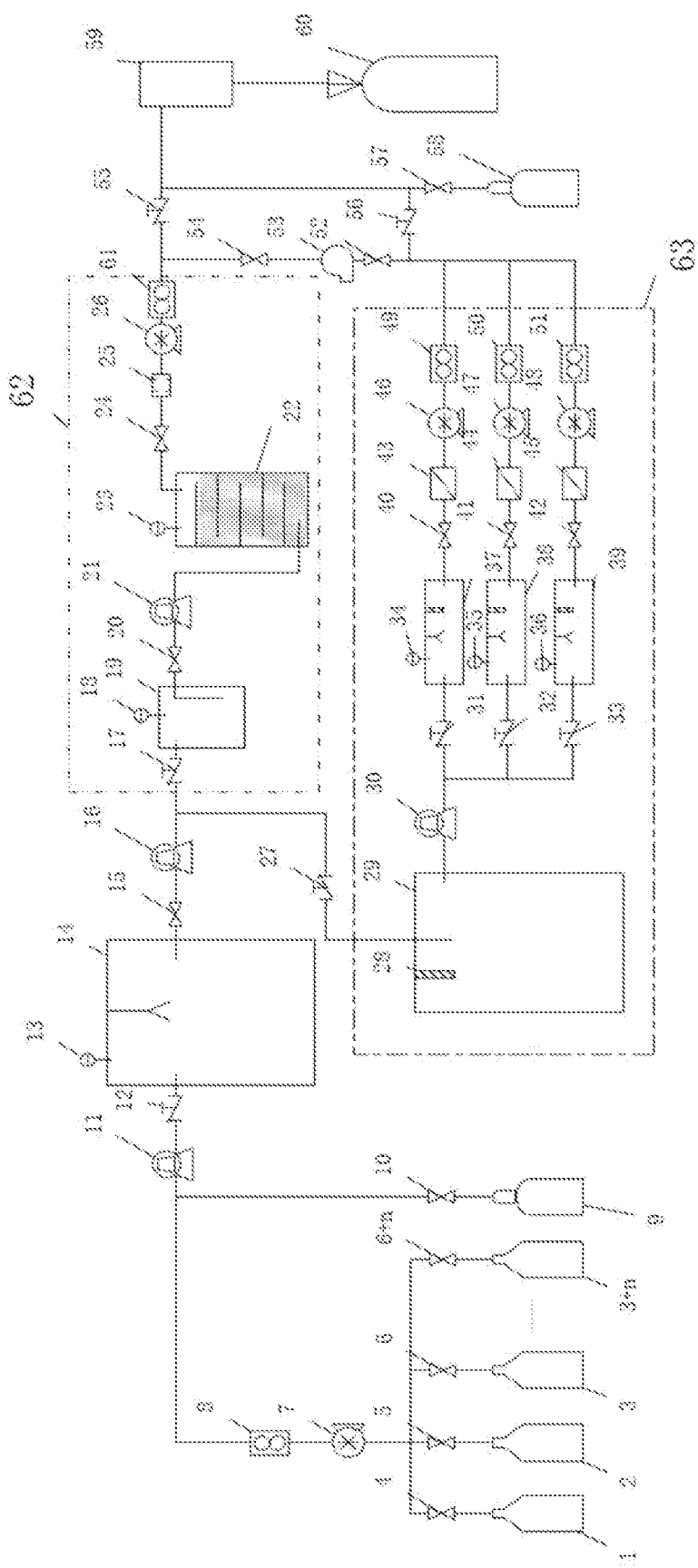
FIG. 1 is a structure diagram of the parallel device for high-precision determination of sulfur solubility under multiple influencing factors in the present invention.
Figure 2:
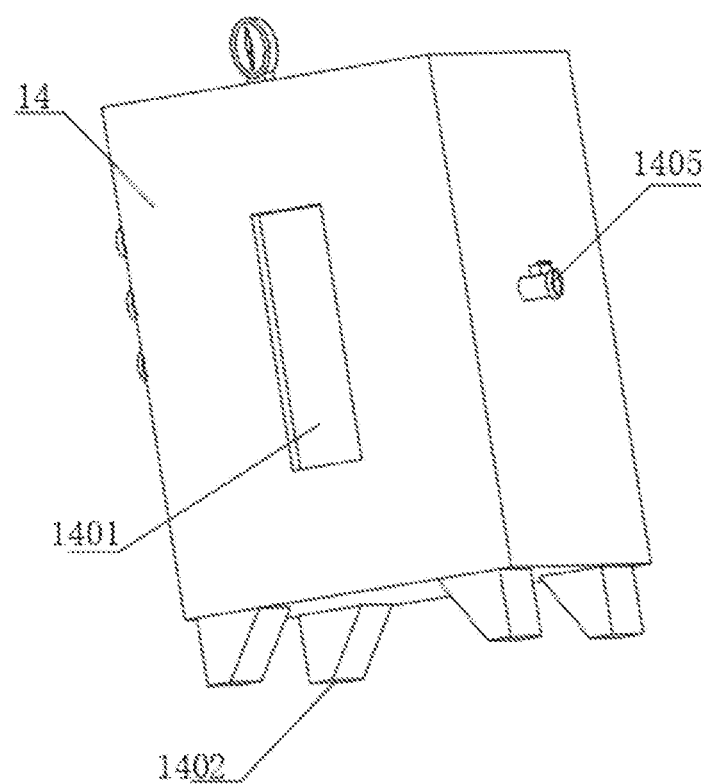
FIG. 2 is a stereoscopic structure diagram of gas sample preparation chamber of the parallel device for high-precision determination of sulfur solubility under multiple influencing factors in the present invention.
Figure 3:
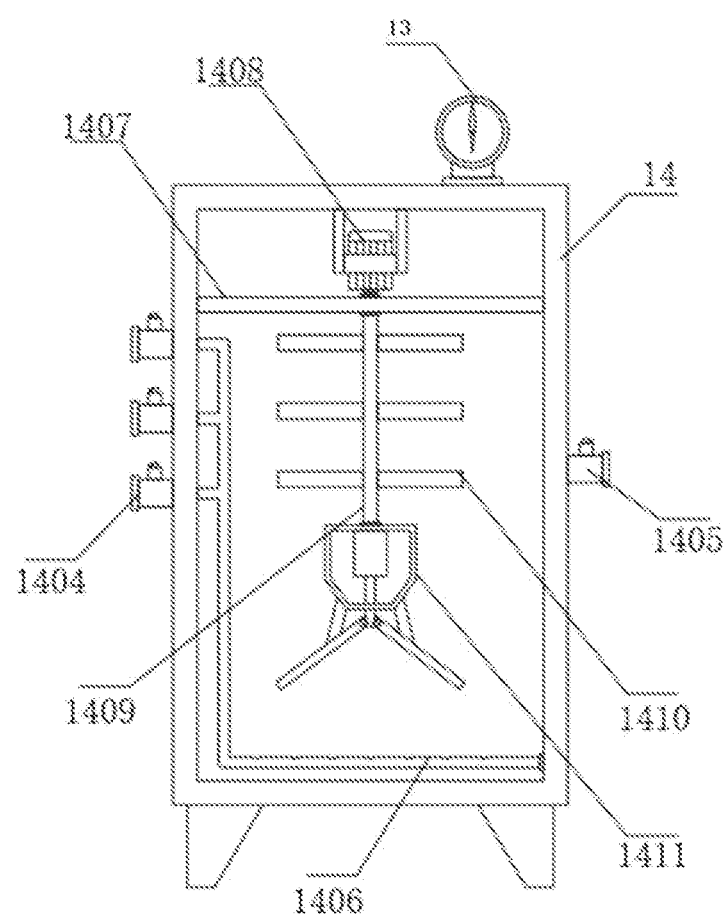
FIG. 3 is a structure diagram from the front view of gas sample preparation chamber of the parallel device for high-precision determination of sulfur solubility under multiple influencing factors in the present invention.
Figure 4:
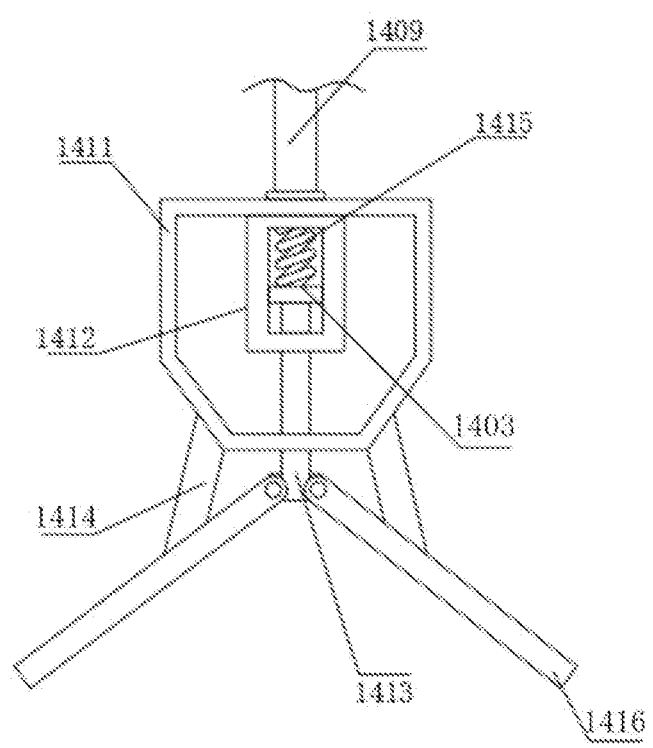
FIG. 4 is a local structure diagram of stirring device of the parallel device for high-precision determination of sulfur solubility under multiple influencing factors in the present invention.

On the one hand, as shown in FIGS. 1-4, the prevent invention provides a parallel device for high-precision determination of sulfur solubility under multiple influencing factors, comprising a sample preparation system, an elemental sulfur absorption system, an elemental sulfur saturation system, a sulfur content determination system, a vacuum pumping system, and a nitrogen filling and replacement system. The elemental sulfur absorption system is used to absorb the elemental sulfur of sour gas, and arranged in an incubator I (62). The elemental sulfur saturation system, arranged in an incubator II (63), comprises multiple elemental sulfur saturation subsystems arranged in parallel, and the subsystems are used to saturate sour gas under different temperature and pressure conditions at the same time. The elemental sulfur absorption system is arranged in parallel with the elemental sulfur saturation system, with the input terminals of both are connected with the output terminal of the sample preparation system, and the output terminals of both connected with the input terminal of the sulfur content determination system. The sulfur content determination system is used to determine the total sulfur content of the elemental sulfur saturation system, and calibrate the elemental sulfur content in the sour gas after the elemental sulfur absorption system absorbs the elemental sulfur under the same conditions as the elemental sulfur saturation system. The vacuum pumping system is used to make the whole device vacuum to remove impurities. The nitrogen filling and replacement system is used to fill the entire device with nitrogen to test the air tightness of the device and blow the elemental sulfur precipitated in the pipe into the sulfur content determination system.

In a specific embodiment, the sample preparation system comprises gas cylinders, gas cylinder valves, a constant speed and constant pressure (CSCP) pump I (7), a gas flowmeter I (8), a gas booster pump I (11), a one-way valve I (12), a gas sample preparation chamber (14), a gas sample preparation chamber valve (15), and a gas booster pump II (16), which are connected in turn. The gas cylinders include a hydrogen sulfide cylinder (1), a carbon dioxide cylinder (2), and a methane cylinder (3) arranged in parallel. The gas cylinder valves include a hydrogen sulfide cylinder valve (4), a carbon dioxide cylinder valve (5), and a methane cylinder valve (6). The gas sample preparation chamber (14) is connected with a pressure gauge I (13). It should be noted that the gas cylinders and the gas cylinder valves can be added with corresponding parallel pipelines of other gas cylinders in addition to the three parallel pipelines arranged in the above embodiments;

The elemental sulfur absorption system comprises a one-way valve II (17), an intermediate container (19), an intermediate container valve (20), a gas booster pump III (21), an elemental sulfur absorption chamber (22), an absorption chamber valve (24), a gas dryer (25), a CSCP pump II (26), and a gas flowmeter II (61), which are connected in turn. The intermediate container (19) is connected to a pressure gauge II (18), the elemental sulfur absorption chamber (22) is connected to a pressure gauge III (23), and the elemental sulfur absorption chamber (22) is provided with a chemical agent for absorbing elemental sulfur;

The elemental sulfur saturation system comprises a one-way valve III (27), a gas preheating chamber (29), a gas booster pump IV (30), three groups of elemental sulfur saturation subsystems arranged in parallel, which are connected in turn. Each group of sulfur saturation subsystem comprises a one-way valve, an HTHP sample preparation chamber, a sample preparation chamber valve, a sulfur powder filter, a CSCP pump, and a gas flowmeter, which are connected in turn. The gas preheating chamber (29) is provided with an electromagnetic strip heater I (28), the HTHP sample preparation chamber is provided with an electromagnetic strip heater H. and the HTHP sample preparation chamber is connected with a pressure gauge; specifically:

One elemental sulfur saturation subsystem includes a one-way valve IV (31), an HTHP sample preparation chamber I (37), a sample preparation chamber valve I (40), a sulfur powder filter I (43), a CSCP pump III (46), and a gas flowmeter III (49), which are connected in turn; the HTHP sample preparation chamber I is connected with a pressure gauge IV (34);

Another elemental sulfur saturation subsystem includes a one-way valve V (32), an HTHP s sample preparation chamber II (38), a sample preparation chamber valve II (41), a sulfur powder filter II (44), a CSCP pump IV (47), and a gas flowmeter IV (50), which are connected in turn; the HTHP sample preparation chamber II is connected with a pressure gauge V (35);

The other elemental sulfur saturation subsystem includes a one-way valve VI (33), an HTHP sample preparation chamber III (39), a sample preparation chamber valve III (42), a sulfur powder filter III (45), a CSCP pump V (48), and a gas flowmeter V (51), which are connected in turn; the HTHP sample preparation chamber III is connected with a pressure gauge VI (36);

The sulfur content determination system comprises a fluorescence sulfur analyzer (59) and a tail gas treatment device (60) which are connected in turn; the input terminal of fluorescence sulfur analyzer (59) is connected with the output terminal respectively of elemental sulfur absorption system and elemental sulfur saturation system;

The vacuum pumping system comprises a vacuum pump (53) of which the output terminal is connected with the output terminal of the elemental sulfur absorption system by a pipeline I that is provided with a vacuum pump valve I (54); the output terminal of the vacuum pump (53) is connected with the output terminal of the elemental sulfur saturation system by a pipeline II which is provided with a vacuum pump valve II (52);

The nitrogen filling and replacement system comprises a nitrogen cylinder I (9) and a nitrogen cylinder II (58); the nitrogen cylinder I (9) is used to fill the entire device with nitrogen to test the air tightness of the device, and the nitrogen cylinder II (58) is used to blow the elemental sulfur precipitated in the pipe into the sulfur content determination system; the nitrogen cylinder I (9) is connected with the pipeline between the gas flowmeter (8) and the gas booster pump I (11) via a pipeline III which is provided with a nitrogen valve I (10); the nitrogen cylinder II (58) is connected with the output terminal respectively of the elemental sulfur absorption system and the elemental sulfur saturation system through a pipeline IV which is provided with a nitrogen valve II (57).

In a specific embodiment, the elemental sulfur absorption chamber (22) is internally provided with carbon disulfide. Optionally, the elemental sulfur absorption chamber (22) is further provided with cross slabs to enable more adequate absorption of elemental sulfur.

In a specific embodiment, the effective volumes of the gas preparation chamber (14), the HTHP preparation chamber, the intermediate container (19), and the elemental sulfur absorption chamber (22) are reduced in turn, and the volume of the next container is not greater than ⅓ of that of the previous container.

In a specific embodiment, the sample preparation chamber (14) comprises a seal housing provided with a stirring device, the side wall of the seal housing is provided with an intake pipe (1404) and an outlet pipe (1405) which are connected inside of the seal housing, the sealing shell is internally provided with a connecting pipe (1406) with one terminal connected with the output terminal of the intake pipe (1404), and the connecting pipe (1406) is provided with a plurality of evenly distributed air vents.

Optionally, the seal housing is provided with a fixed base (1402) at the bottom, and a transparent window (1401) on the side wall; the connecting pipe (1406) comprises a vertical segment and a horizontal segment which are connected; the inlet terminal of vertical segment is connected with the output terminal of the intake pipe (1404), and the air vents are arranged on the upper surface of horizontal segment of the connecting pipe (1406).

In a specific embodiment, the stirring device comprises a motor (1408), the output terminal of the motor (1408) is provided with a rotating rod (1409) of which the side wall is equipped with a plurality of stirring blades (1410) and the bottom is connected with the top of the link block (1411); the left and right ends of the bottom of the link block (1411) are respectively provided with a limit rod (1414) that is fitted with a fixed cylinder (1412) internally, the fixed barrel (1412) is provided with a vertical rod (1413) with other terminals passing through the fixed cylinder (1412) and extending towards the link block (1411), the top of the vertical rod (1413) is provided with a limit slider (1403) that is provided with a spring (1415), the left and right ends of the bottom of the vertical rod (1413) are hinged with the movable plates (1416), the upper surfaces of the two movable plates (1416) are respectively designed with a chute (not shown in the figure), and the limit rod (1414) is limited to slide in the chute.

The stirring device of the above embodiment can drive the structure at the rotating rod bottom to slide up and down the movable plates (1416) under the combined action of the limit rod (1414), the limit slider (1403), the spring (1415) and the vertical rod (1413), etc., so as to change the mixing flow direction of the gas in the sample preparation chamber (14), increase the mixing rate of the gas in the sample preparation chamber (14), thereby improving the detection effect.

Optionally, the seal housing is provided with a support plate (1407), and the motor (1408) is arranged on the support plate (1407).

On the other hand, the present invention also provides a method for high-precision determination of sulfur solubility under multiple influencing factors, and the parallel device for high-precision determination of sulfur solubility under multiple influencing factors described in any one of the above items is used for determination, including the following steps:

Prepare the sour gas to be determined with the sample preparation system, and then determine the sulfur content I of sour gas to be determined after sulfur absorption and the volume of hydrogen sulfide gas through the path of sample preparation system, elemental sulfur absorption system and sulfur content determination system;

Prepare the same sour gas to be determined with the sample preparation system, and then determine the sulfur content II of sour gas to be determined after sulfur saturation at different temperatures and pressures through the path of sample preparation system, elemental sulfur saturation system and sulfur content determination system;

Work out the solubility of the sour gas to be determined by calculating the sulfur content I, sulfur content 11 and the volume of hydrogen sulfide gas.

Preferably, the solubility is calculated by the following equation:

$$R = \frac{M - m}{V} \quad (1)$$

Where, R is the solubility of sour gas to be determined; m is the sulfur content I of sour gas to be determined after removal of elemental sulfur; M is the sulfur content II of sour gas to be determined after the saturation of sulfur monomer; V is the volume of sour gas sample.

In an embodiment where the present invention is specifically used to test the sulfur solubility of sour gas, the following steps are included.

(1) Check the air tightness of the device

Close the one-way valve VIII (55), one-way valve IX (56), vacuum pump valve II (52), vacuum pump valve I (54), hydrogen sulfide cylinder valve (4), carbon dioxide cylinder valve (5), and methane cylinder valve (6), open the nitrogen valve 1 (10), fill the whole device with $N_2$, close nitrogen valve 1 (10), and observe whether the value of each pressure gauge is stable; if it is stable, the air tightness of the whole device is sound.

(II) Test the sulfur content of mixed gas after sulfur absorption

Step 1: Open the vacuum pump valve II (52), vacuum pump valve I (54) and other valves, start the vacuum pump (53), pump out the $N_2$ from each vessel and pipeline until there is vacuum shown by the pressure gauge, and then close all valves of the device.

Step 2: According to the known gas composition of sour gas, allocate the gas volume of each gas sample, open the valve (4) and one way valve I (12) of the hydrogen sulfide cylinder, open the CSCP pump I (7) to maintain the gas flow rate constant, observe the volume of hydrogen sulfide passing through the gas flowmeter I (8), pump the gas sample into the sample preparation chamber (14) with the gas booster pump I (11), and close the hydrogen sulfide cylinder valve (4) after reaching the predetermined volume.

Step 3: Open the carbon dioxide cylinder valve (5), pump $CO_2$ gas into the sample preparation chamber (14) according to the allocated volume, and close the carbon dioxide cylinder valve (5) after reaching the predetermined volume.

Step 4: Open the methane cylinder valve (6), pump $CH_4$ gas into the sample preparation chamber (14) according to the allocated volume, and close the methane cylinder valve (6) after reaching the predetermined volume.

Step 4: Open the valves (6+n) of other gas sample cylinders, pump other gas in sample cylinders (3+n), into the sample preparation chamber (14) according to the allocated volume, and close valves (6+n) of other gas sample cylinders after reaching the predetermined volume.

Step 5: Start the stirring device in the gas sample preparation chamber to fully and evenly mix the gas, record the current pressure of the pressure gauge I (13), open the sample preparation chamber valve (15) and the one-way valve II (17), and pump the mixed gas in the sample preparation chamber (14) into the middle container (19) until the pressure is consistent with the maximum pressure in the preset experiment.

Step 6: Open the intermediate vessel valve (20), pump the gas into the elemental sulfur absorption chamber (22) containing carbon disulfide solution with the gas booster pump III (21) until the air pressure in the elemental sulfur absorption chamber (22) is consistent with the first.
group of pressure $P_1$ in the preset experiment, and close the intermediate vessel valve (20).
Step 7: Open the absorption chamber valve (24) and the one-way valve VIII (55), fill the sour gas sample into the fluorescence sulfer analyzer (59) after passing the gas dryer (25) and the gas flowmeter II (26), record the current reading $V_1$ of gas flowmeter, and determine the mass $m_1$ of elemental sulfur generated by the current gas sample at that volume.

Repeat Steps 6 and 7, change the air pressure in the elemental sulfur absorption chamber (22), and determine the elemental sulfur mass $m_2$ and $m_3$ under different pressures in the preset experiment. This step can be ignored if there is no sulfur solubility determination under different pressures in the preset experiment.

(III) Test the sulfur content in the gas after sulfur powder saturation

Step 8: Open the sample preparation chamber valve (15) and the one-way valve III (7), pump the mixed gas in the gas preparation chamber (14) into the preheating chamber (29), and preheat the gas to the set temperature with the electromagnetic strip heater I (32).

Step 9: Open the one-way valve IV (31), pump the preheated gas sample into the high-temperature and high-pressure (HTHP) sample preparation chamber I (37) by the gas booster pump IV (30) until the pressure gauge IV reaches the preset experimental pressure $P_1$, close the one-way valve IV (31), heat the gas to the preset experimental temperature $T_1$ with the electromagnetic strip heater in the HTHP sample preparation chamber I (37), and start the stirring device, and evenly mix the sulfur powder and sour gas.

Step 10: Open the one-way valve V (32), pump gas into the HTHP sample preparation chamber II (38) until the pressure gauge V (35) reaches the preset pressure $P_2$, raise the temperature to $T_2$, and mix sulfur powder and sour gas sample evenly.

Step 11: Open the one-way valve VI (33), pump gas into the HTHP sample preparation chamber III (39) until the pressure gauge VI (36) reaches the preset pressure $P_3$, raise the temperature to $T_3$, and mix sulfur powder and sour gas sample evenly.

Step 12: Open the sample preparation chamber valve I (40) and the one-way valve IX (56), pump the gas into the fluorescence sulfur analyzer (59) at uniform pressure by the CSCP pump III (46), and close the valve I (40) of the sample preparation chamber when the value of gas flowmeter III (49) reaches $V_1$.

Step 13: Open the nitrogen valve II (57), blow the sulfur powder precipitated in the pipeline into the fluorescence sulfur analyzer (59) with nitrogen in the nitrogen cylinder II (58), and then close the valve to determine the sulfur content $M_1$ of the current gas sample.

Step 14: Open the valve II (41) of the sample preparation chamber, pump the gas into the fluorescence sulfur analyzer (59) at uniform pressure by the CSCP pump IV (47), and close the valve II (41) of the sample preparation chamber when the value of gas flowmeter IV (50) reaches $V_1$.

Step 15: Open the nitrogen valve II (57), blow the sulfur powder precipitated in the pipeline into the fluorescence sulfur analyzer (59) with nitrogen in the nitrogen cylinder II (58), and then close the valve to determine the sulfur content $M_2$ of the current gas sample.

Step 16: Open the valve III (42) of the sample preparation chamber, pump the gas into the fluorescence sulfur analyzer (59) at uniform pressure by the CSCP pump V (48), and close the valve III (42) of the sample preparation chamber when the value of gas flowmeter V (51) reaches $V_1$.

Step 17: Open the nitrogen valve II (57), blow the sulfur powder precipitated in the pipeline into the fluorescence sulfur analyzer (59) with nitrogen in the nitrogen cylinder II (58), and then close the valve to determine the sulfur content $M_3$ of the current gas sample.

Change the gas components in sample preparation chamber (14), repeat the above steps, and determine the sulfur solubility in sour gas under different gas component conditions.

The above are only the preferred embodiments, which are not intended to limit the present invention in any form.

Although the present invention has been disclosed as above with preferred embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A parallel device for high-precision determination of sulfur solubility under multiple influencing factors, comprising a sample preparation system, an elemental sulfur absorption system, an elemental sulfur saturation system, a sulfur content determination system, a vacuum pumping system, and a nitrogen filling and replacement system; the elemental sulfur absorption system is used to absorb the elemental sulfur of sour gas, and arranged in an incubator; the elemental sulfur saturation system, arranged in a second incubator, comprises multiple elemental sulfur saturation subsystems arranged in parallel, and the subsystems are used to saturate sour gas under different temperature and pressure conditions at the same time; the elemental sulfur absorption system is arranged in parallel with the elemental sulfur saturation system, with the input terminals of both are connected with the output terminal of the sample preparation system, and the output terminals of both connected with the input terminal of the sulfur content determination system; the sulfur content determination system is used to determine the total sulfur content of the elemental sulfur saturation system, and is used to calibrate the elemental sulfur content in the sour gas after the elemental sulfur absorption system absorbs the elemental sulfur under the same conditions as the elemental sulfur saturation system; the vacuum pumping system is used to make the whole device vacuum to remove impurities; the nitrogen filling and replacement system is used to fill the entire device with nitrogen to test the air tightness of the device and blow the elemental sulfur precipitated in the pipe into the sulfur content determination system.

2. The parallel device for high-precision determination of sulfur solubility under multiple influencing factors according to claim 1, wherein the sample preparation system comprises gas cylinders, gas cylinder valves, a constant speed and constant pressure (CSCP) pump I (7), a gas flowmeter I, a gas booster pump I, a one-way valve I, a gas sample preparation chamber, a gas sample preparation chamber valve, and a gas booster pump II, which are connected in turn; the gas cylinders comprise a hydrogen sulfide cylinder, a carbon dioxide cylinder, and a methane cylinder arranged in parallel; the gas cylinder valves comprise a hydrogen sulfide cylinder valve, a carbon dioxide cylinder valve, and a methane cylinder valve; the gas sample preparation chamber is connected with a pressure gauge I;

The elemental sulfur absorption system comprises a one-way valve II, an intermediate container, an intermediate container valve, a gas booster pump III, an elemental sulfur absorption chamber, an absorption chamber valve, a gas dryer, a CSCP pump II, and a gas flowmeter II, which are connected in turn; the intermediate container is connected to a pressure gauge II, the elemental sulfur absorption chamber is connected to a pressure gauge III, and the elemental sulfur absorption chamber is provided with a chemical agent for absorbing elemental sulfur;

The elemental sulfur saturation system comprises a one-way valve III, a gas preheating chamber, a gas booster pump N, three groups of elemental sulfur saturation subsystems arranged in parallel, which are connected in turn; each group of sulfur saturation subsystem comprises a one-way valve, an HTHP sample preparation chamber, a sample preparation chamber valve, a sulfur powder filter, a CSCP pump, and a gas flowmeter, which are connected in turn; the gas preheating chamber is provided with an electromagnetic strip heater I, the HTHP sample preparation chamber is provided with an electromagnetic strip heater II, and the HTHP sample preparation chamber is connected with a pressure gauge;

The sulfur content determination system comprises a fluorescence sulfur analyzer and a tail gas treatment device which are connected in turn; the input terminal of fluorescence sulfur analyzer is connected with the output terminal respectively of elemental sulfur absorption system and elemental sulfur saturation system;

The vacuum pumping system comprises a vacuum pump of which theft input terminal is connected with the output terminal of the elemental sulfur absorption system by a pipeline I that is provided with a vacuum pump valve I; the input terminal of the vacuum pump is connected with the output terminal of the elemental sulfur saturation system by a pipeline II which is provided with a vacuum pump valve II;

The nitrogen filling and replacement system comprises a nitrogen cylinder I and a nitrogen cylinder II; the nitrogen cylinder I is used to fill the entire device with nitrogen to test the air tightness of the device, and the nitrogen cylinder II is used to blow the elemental sulfur precipitated in the pipe into the sulfur content determination system; the nitrogen cylinder I is connected with the pipeline between the gas flowmeter and the gas booster pump I via a pipeline III which is provided with a nitrogen valve I; the nitrogen cylinder II is connected with the output terminal respectively of the elemental sulfur absorption system and the elemental sulfur saturation system through a pipeline N which is provided with a nitrogen valve II.

3. The parallel device for high-precision determination of sulfur solubility under multiple influencing factors according to claim 2, wherein the elemental sulfur absorption chamber is internally provided with carbon disulfide.

4. The parallel device for high-precision determination of sulfur solubility under multiple influencing factors according to claim 2, wherein the effective volumes of the gas preparation chamber, the HTHP preparation chamber, the intermediate container, and the elemental sulfur absorption chamber are reduced in turn, and the volume of the next container is not greater than $\frac{1}{3}$ of that of the previous container.

5. The parallel device for high-precision determination of sulfur solubility under multiple influencing factors according to claim 2, wherein the sample preparation chamber comprises a seal housing provided with a stirring device, the side wall of the seal housing is provided with an intake pipe and an outlet pipe which are connected inside of the seal housing, the sealing shell is internally provided with a connecting pipe with one terminal connected with the output terminal of the intake pipe, and the connecting pipe is provided with a plurality of evenly distributed air vents.

6. The parallel device for high-precision determination of sulfur solubility under multiple influencing factors according to claim 5, wherein the seal housing is provided with a fixed base at the bottom.

7. The parallel device for high-precision determination of sulfur solubility under multiple influencing factors according to claim 5, wherein the seal housing is provided with a transparent window on the side wall.

8. The parallel device for high-precision determination of sulfur solubility under multiple influencing factors according to claim 5, wherein the stirring device comprises a motor, the output terminal of the motor is provided with a rotating rod of which the side wall is equipped with a plurality of stirring blades and the bottom is connected with the top of the link block; the left and right ends of the bottom of the link block are respectively provided with a limit rod that is fitted with a fixed cylinder internally, the fixed barrel is provided with a vertical rod with other terminals passing through the fixed cylinder and extending towards the link block, the top of the vertical rod is provided with a limit slider that is provided with a spring, the left and right ends of the bottom of the vertical rod are hinged with the movable plates, the upper surfaces of the two movable plates are respectively designed with a chute, and the limit rod is limited to slide in the chute.

9. A method for high-precision determination of sulfur solubility under multiple influencing factors, the parallel device for high-precision determination of sulfur solubility under multiple influencing factors described in claim 1 is used for determination, comprising the following steps:

Prepare the sour gas to be determined with the sample preparation system, and then determine the sulfur content I of sour gas to be determined after sulfur absorption and the volume of hydrogen sulfide gas through the path of sample preparation system, elemental sulfur absorption system and sulfur content determination system;

Prepare the same sour gas to be determined with the sample preparation system, and then determine the sulfur content II of sour gas to be determined after sulfur saturation at different temperatures and pressures through the path of sample preparation system, elemental sulfur saturation system and sulfur content determination system;

Work out the solubility of the sour gas to be determined by calculating the sulfur content I, sulfur content II and the volume of hydrogen sulfide gas.

10. The method for high-precision determination of sulfur solubility under multiple influencing factors according to claim 9, wherein the solubility is calculated by the following $$R = \frac{M - m}{V} \quad (1)$$

Where, R is the solubility of sour gas to be determined; m is the sulfur content I of sour gas to be determined after removal of elemental sulfur; M is the sulfur content II of sour gas to be determined after the saturation of sulfur monomer; V is the volume of sour gas sample.

* * * * *